United States Patent [19]

Kolbe

[11] Patent Number: 5,276,141
[45] Date of Patent: Jan. 4, 1994

[54] PROCESS FOR PURIFYING A HIGHLY GLYCOSYLATED PROTEIN

[75] Inventor: Hanno Kolbe, Illkirch, France

[73] Assignee: Transgene S.A., Strasbourg, France

[21] Appl. No.: 835,392

[22] Filed: Feb. 14, 1992

[30] Foreign Application Priority Data

Feb. 15, 1991 [FR] France ................. 91 01830

[51] Int. Cl.⁵ .................. C07K 3/18; C07K 3/20; C07K 15/00; C07K 15/14
[52] U.S. Cl. ...................... 530/395; 530/396; 530/397; 530/398; 530/418; 530/419; 530/420; 435/814; 435/816
[58] Field of Search ............ 530/395, 396, 397, 398, 530/418, 419, 420; 435/814, 816

[56] References Cited

U.S. PATENT DOCUMENTS

| | | | |
|---|---|---|---|
| 3,947,324 | 3/1976 | Lakshminarayanan | 435/192 |
| 4,704,274 | 11/1987 | Sakuma et al. | 530/413 |
| 4,774,086 | 9/1988 | Quentin-Millet et al. | 435/822 |
| 4,798,886 | 1/1989 | Kato et al. | 530/350 |
| 4,855,284 | 8/1989 | Emoedi | 530/396 |
| 4,992,372 | 2/1991 | Pokora et al. | 435/816 |
| 5,101,014 | 3/1992 | Burns et al. | 530/350 |

FOREIGN PATENT DOCUMENTS 2277043 3/1988 European Pat. Off. .
0321606 6/1989 European Pat. Off. .

OTHER PUBLICATIONS

Chemical Abstract No. 102224a, vol. 96 (1982), p. 536.
French Search Report, Application No. FR 9101830, dated Feb. 15, 1991.
FEBS Letters, vol. 80, No. 2 (1977), pp. 351–354.
Sulkowski, Eugene. "Immobilized Metal Ion Affinity Chromatography of Proteins", Protein Purification: Micro to Macro, publ. by Alan R. Liss, Inc.: New York. (1987), pp. 149–162.

Primary Examiner—Ronald W. Griffin
Attorney, Agent, or Firm—Burns, Doane, Swecker & Mathis

[57] ABSTRACT

The invention proposes a process for purifying a highly glycosylated protein from a crude preparation which comprises the action (i) of adding to said preparation a divalent metal ion in a sufficient amount in order to form a mixture which precipitates and (ii) after precipitation, of harvesting said protein from the mixture supernatant.

17 Claims, No Drawings

PROCESS FOR PURIFYING A HIGHLY GLYCOSYLATED PROTEIN

The present invention relates to a process for purifying a highly glycosylated protein.

By definition, a protein essentially consists of a chain of amino acids. Furthermore, in many cases this chain contains a more or less substantial amount of carbohydrate groups of varying sizes. Proteins containing such groups are called glycosylated proteins.

Generally, it is known that metals such as zinc, copper, cobalt, calcium or nickel can form complexes with proteinaceous compounds. As a result, these metals are commonly used in processes for purifying proteins either as coupling agents for example during affinity chromatography or to precipitate proteins in a liquid medium.

Surprisingly, it has now been found that highly glycosylated proteins are not capable of forming complexes with the abovementioned metals.

Consequently, the invention proposes a process for purifying a highly glycosylated protein from a crude preparation derived from a culture of eukaryotic cells, said process comprising the action (i) of adding to said preparation a divalent metal ion in a sufficient amount in order to form a mixture which precipitates and (ii) after precipitation, of harvesting said protein from the mixture supernatant.

Highly glycosylated protein is understood as meaning a protein with a glycosylation level of not less than 20%, preferably of not less than 30% and most preferably not less than 40%. The level of glycosylation is the ratio between the glycosylation mass and the total mass of the protein expressed as a percentage. This glycosylation level may be determined by comparing the mass of a glycosylated protein with that of its nonglycosylated form obtained after treating with an endoglucosidase (endoglucosidase F or H sold for example by Boehringer) according to the conditions specified by the supplier. The relative masses of the glycosylated and nonglycosylated forms are determined after migration on SDS-PAGE gel.

Alternatively, if the amino acid sequence of the glycosylated protein is known, the mass of the peptide chain may be calculated. Quantitation of the sugars may be carried out in parallel after hydrazinolysis of the glycosylated protein.

Fetuin, the glycoproteins gp120 and gp160 of the HIV virus, mucins, human interleukin-2, glycophorin-like proteins and acid alpha-1-glycoprotein which is present in the serum, are for example proteins which naturally present a high glycosylation level. For the purposes of the present invention, the protein which it is desired to purify may possess a glycosylation profile which is homogeneous (glycosylation covering the entire peptide chain) or heterogeneous (glycosylation localized at certain areas of the peptide chain). Preferably, the glycosylation is homogeneous.

The crude preparation from which it is desired to purify a highly glycosylated protein is derived from a culture of eukaryotic cells capable of synthesizing this protein. The composition of the culture medium is not critical and may contain any suitable component. The various methods which enable the synthesis of a protein to be obtained using the recombinant route are known, the basic element to be introduced inside a cell being the expression cassette designed for the synthesis of this protein. Advantageously, an expression cassette comprises a DNA fragment encoding a precursor of the highly glycosylated protein (signal peptide + mature protein) placed under the control of elements required for its expression.

Within the framework of the present invention, a highly glycosylated protein is advantageously purified from an acellular extract derived from a culture of eukaryotic cells, preferably a yeast or mammalian cell culture. This acellular extract may be a cell culture supernatant in the case where the protein is either secreted in the culture medium or the cells are lysed by a virus during the culture. Alternatively, the acellular extract may also be obtained from a cell suspension subjected to a chemical, mechanical or enzymatic type lytic treatment and whose liquid element is then separated from the cell debris.

For use within the framework of the present invention, a divalent metal ion is advantageously selected from $Zn^{2+}$, $Cu^{2+}$, $Co^{2+}$, $Ni^{2+}$ and $Ca^{2+}$. Preferably, this metal ion is added in the form of a salt. $ZnCl_2$, $CuSO_4$, $CoSO_4$, $NiSO_4$ and $CaCl_2$ may be mentioned by way of example.

Generally, the amount of metal ion which should be added to the crude preparation depends on the very nature of the metal ion and the components which it is desired to remove. A person skilled in the art will obviously be able to adjust the final optimum concentration as a function of the specific parameters. However, it is specified that the contaminants present in the crude preparation may precipitate as soon as the metal ion is added to a final concentration of not less than 10 mM, advantageously of not less than 40 mM, preferably of not less than 60 mM and most preferably of not less than 80 mM. Although it is possible to add the metal ion in bulk, it is generally not necessary to exceed a final concentration of about 100 to 120 mM.

Advantageously, the process according to the invention is carried out at an acid or close to neutral pH, in general of 7.5 or less than 7.5. Preferably, the process is carried out at a slightly acid pH of between 6 and 7.

After precipitation, the supernatant is advantageously harvested by centrifugation of the mixture and successive decantation.

Such a process enables the virions, which may be present in the crude preparation, to be removed in a simple and efficient manner. If necessary, purification of the highly glycosylated protein present in the precipitation supernatant may subsequently be carried out in a more elaborate manner using a variety of methods.

According to a particular aspect, the invention proposes a process for purifying the HIV virus gp120 or a soluble variant of the HIV virus gp160. Some variants of gp160 are described for example in patent application EPA 245 136. The gp120 or a soluble variant of gp160 may in particular be produced using recombinant DNA techniques. A vector designed for this production is for example a plasmid or a vaccinia virus in whose genome is inserted a DNA fragment encoding gp120 or a soluble variant of gp160, this fragment being placed under the control of the appropriate regions permitting its expression (transcription and translation).

Finally, the invention relates, alternatively, to a process for purifying or concentrating a poxvirus from a preparation, for example the supernatant of a cell lysate obtained by infecting an infected cell culture with said poxvirus, the process comprising the action (i) of adding to said preparation a divalent metal ion in a sufficient amount in order to form a mixture which precipitates and (ii), after precipitation, of harvesting said poxvirus in the form of a precipitate.

EXAMPLE 1

A. Production of gp120 from HIV1-BRU in a Culture of Cells Infected with a Recombinant Vaccinia Virus BHK-21 cells are cultured in a GMEM medium (Gibco) supplemented with 10% of fetal calf serum (FCS). When the cells are confluent ($5.8\times10^6$ cells/ml), the culture medium is removed and the cellular lawn is washed twice with 50 ml of PBS (Dubelcco's phosphate buffer salt; Seromed). Fresh GMEM medium without FCS is then added. The vaccinia virus VVTG1132, described in patent application EPA 245 136, is then added to an infectivity of $10^{-1}$ pfu (plaque forming units), and the infection is maintained for 72 h. The lysate is then centrifuged for 20 min at 10,000 g in order to remove the cell debris, and the supernatant, containing inter alia gp120 and the virions, is recovered.

B. Purification of gp120

1.3 ml of a 1M solution of zinc chloride ($ZnCl_2$) are added to 20 ml of culture supernatant obtained as described above in order to obtain a final $ZnCl_2$ concentration of 60 mM. The pH of this mixture is about 6.8. The mixture is left on ice for 1 h and then the precipitation supernatant is recovered after centrifugation at 3000 r/min for 20 min in a Heraeus RF Minifuge centrifuge. The supernatant contains the initial amount of gp120 found in the culture supernatant but no longer contains, inter alia, virions. For analysis, quantitation of the total proteins and gp120 as well as titration of the vaccinia virus are carried out using the methods described below. These quantitations are carried out in parallel on the crude culture supernatant not treated with $ZnCl_2$.

Quantitation of the total proteins is carried out as follows according to the Biuret method described by Kadenbach B, Biochem. Z. (1966) 344: 49-75: 3 ml of supernatant obtained after precipitation with $ZnCl_2$ are treated with 300 μl of 3M trichloroacetic acid (TCA). After 1 h at 20° C., the proteins are precipitated and the solution is centrifuged for 20 min at 3000 revolutions per minute in a Heraus RF Minifuge centrifuge. The supernatant is removed and the pellet is taken up in 1 ml of Biuret solution (12 mM of copper sulfate ($CuSO_4$, $5H_2O$), 31.89 mM of potassium sodium tartrate (KNa tartrate), 200 mM of sodium hydroxide (NaOH) and 30.12 mM of potassium iodide (IK)). After 15 min, the proteins are dissolved in the Biuret solution and 1 ml of Milli-Q water is added. The optical density (OD) at 546 nm is measured against air in 1 cm cuvettes. The OD is also measured on an absorption blank in which only the Biuret solution and water were added. The value of the OD is noted OD.E for the samples or OD.T for the absorption blank. 50 to 100 mg of potassium cyanide (KCN) are then added to the cuvettes and mixed into the solution using a spatula. After 2 to 5 min, the OD at 546 nm is measured and the value is noted OD.E/KCN for the samples and OD.T/KCN for the absorption blank. The total amount of proteins in the samples (Q) is then calculated using the following formula:

$$Q=7\times(DO.E-DO.E/KCN)-(DO.T-DO.T/KCN)$$

The quantitation of gp120 is carried out according to the ELISA test using two anti-gp120 monoclonal antibodies as first and second antibodies, the second being biotinylated. The margin of error associated with such a method of estimation is of the order of ±20%.

Titration of the virus is carried out on BHK-21 cells. 2 ml of GMEM medium containing 10% of FCS are inoculated with $10^6$ BHK-21 cells. The culture is carried out 37° C. in 35×10 mM dishes. After 24 h, the medium is removed and 200 μl of a dilution of the vaccinia virus in PBS are added to the cells. The adsorption is carried out for 1 h at 37° C., and then 2 ml of GMEM medium containing 5% of FCS are added and the infection is continued for 24 h at 37° C. The medium is then removed and the cells are stained with 1 ml of neutral red (Gibco). The lysis plaques which remained white are counted.

The results are presented in Table 1 below.

TABLE 1

| Samples | Concentration of total proteins (μg/ml) | Concentration of gp120 (μg/ml) | Titration of the vaccinia virus (pfu/ml) |
|---|---|---|---|
| Culture supernatant | 257 | 0.202 | $10^6$ |
| Supernatant after precipitation with $ZnCl_2$ | 61.3 | 0.206 | 0 |

These results show that the gp120 protein is not precipitated by $ZnCl_2$ whereas most of the contaminant proteins are precipitated. Similarly, the vaccinia virus is removed in the precipitation pellet.

It is therefore possible, using this process, to remove the virions and more than 50% of the contaminant proteins in a single step.

EXAMPLES 2 to 6

An acellular extract containing gp120 is obtained as described in Example 1A. Similarly, gp120 is purified using procedures similar to that presented in Example 1B in which only the final $ZnCl_2$ concentration may vary from 5 mM to 80 mM. The results of these experiments are collated in Table 2 below.

TABLE 2

| | Samples | Total protein concentration (μg/ml) | gp120 variant concentration (μg/ml) | Titration of the vaccinia virus (pfu/ml) |
|---|---|---|---|---|
| Blank | Culture supernatant | 257 | 0.202 | $10^6$ |
| Ex 2 | Supernatant after precipitation with 5 mM of $ZnCl_2$ | 87 | 0.161 | $2\times10^4$ |
| Ex 3 | SuPernatant after precipitation with 10 mM of $ZnCl_2$ | 74 | 0.182 | $10^3$ |
| Ex 4 | Supernatant after precipitation with 20 mM of $ZnCl_2$ | 72 | 0.184 | $5\times10^2$ |
| Ex 5 | Supernatant after precipitation with 40 mM of $ZnCl_2$ | 63 | 0.248 | 50 |
| Ex 6 | Supernatant aftar precipitation with | 69 | 0.254 | <50 |

TABLE 2-continued

| Samples | Total protein concentration (μg/ml) | gp120 variant concentration (μg/ml) | Titration of the vaccinia virus (pfu/ml) |
|---|---|---|---|
| 80 mM of ZnCl₂ | | | |

These experiments show that the contaminant proteins and the vaccinia virus begin to precipitate from 5 mM of ZnCl₂. It is considered that gp120 does not precipitate given the margin of error of ±20% associated with the method of estimation.

EXAMPLE 7

1. 3 ml of a 1 M solution of calcium chloride ($CaCl_2$) are added to 20 ml of culture supernatant obtained as described in Example 1A above in order to obtain a final $CaCl_2$ concentration of 60 mM. The pH of this medium is about 6.8. The mixture is left on ice for 1 h and then the precipitation supernatant is recovered after centrifugation at 3000 r/min for 20 min in a Heraeus RF Minifuge centrifuge. The supernatant contains the initial amount of gp120 found in the culture supernatant but no longer contains, inter alia, virions. For analysis, quantitation of the total proteins and gp120 as well as titration of the vaccinia virus are carried out using the methods described in Example 1B. These quantitations are carried out in parallel on the crude culture supernatant not treated with $CaCl_2$.

The results of these experiments are collated in Table 3 below.

TABLE 3

| Samples | Concentration of total proteins (μg/ml) | Concentration of gp120 (μg/ml) | Titration of the vaccinia virus (pfu/ml) |
|---|---|---|---|
| Culture supernatant | 218 | 0.360 | 1.5 10⁵ |
| Supernatant after precipitation with CaCl₂ | 139 | 0.374 | <100 |

These results show that $CaCl_2$, like $ZnCl_2$, precipitates most of the vaccinia virus while gp120 remains in solution.

EXAMPLES 8 to 10

An acellular extract containing gp120 is obtained as described in Example 1A. Similarly, gp120 is purified using procedures similar to that presented in Example 7 in which only the final $CaCl_2$ concentration may vary from 20 mM to 80 mM. The results of these experiments are collated in Table 4 below.

TABLE 4

| | Samples | Total protein concentration (μg/ml) | gp120 variant concentration (μg/ml) | Titration of the vaccinia virus (pfu/ml) |
|---|---|---|---|---|
| Blank | Culture supernatant | 218 | 0.280 | 1.5 × 10⁵ |
| Ex 8 | Supernatant after precipitation with 20 mM of CaCl₂ | 163 | 0.282 | 7 × 10³ |
| Ex 9 | Supernatant after precipitation with 40 mM of CaCl₂ | 149 | 0.330 | <100 |
| Ex 10 | Supernatant after precipitation with 80 mM of CaCl₂ | 127 | 0.346 | <100 |

These experiments show that the contaminant proteins and the vaccinia virus begin to precipitate from 10 mM of $CaCl_2$.

EXAMPLE 11

An acellular extract containing a soluble variant of gp160 from HIV1-BRU is obtained after infecting BHK-21 cells with the vaccinia virus VVTG1163 described in patent application EPA 245 136, according to the method described in Example 1A.

880 μl of a 1 M solution of $ZnCl_2$ are added to 20 ml of culture supernatant containing the soluble variant of gp160 obtained as described above, in order to obtain a final $ZnCl_2$ concentration of 40 mM. The mixture is left on ice for 1 h and then the precipitation supernatant is recovered after centrifugation at 3000 r/min for 20 min in a Heraeus RF Minifuge centrifuge. The amount of gp160 variant present in the supernatant after precipitation with $ZnCl_2$ is comparable to that found in the culture supernatant; in contrast, most of the contaminant proteins and all the virions are removed.

EXAMPLE 12

CHO cells are transformed with the plasmid pGT3554. This plasmid is obtained by inserting into the plasmid pTG384 (described in patent application FR 2,600,334) previously digested with HindIII and treated with the Klenow fragment from DNA polymerase I, a PstI fragment, treated with Klenow polymerase encoding a soluble variant of HIV-1 BRU gp160, which is derived from a vaccinia vector VVTG 1163 (described in patent application WO 87/6260). The fragment thus cloned is placed under the control of the late major promotor of adenovirus 2.

About 10⁶ cells are inoculated in MEM α 2000 medium (Gibco) supplemented with 10% of dialyzed fetal calf serum, 2 g/l of glucose, 15 mg/l of hypoxanthine, 10 mg/l of thymidine, 250 mg/l of xanthine, 0.2 mg/l of aminopterin, 25 mg/l of mycophenolic acid and 2 mM of glutamine, and then cultured for 3 days at 37° C. under an atmosphere charged with 5% $CO_2$. The medium is then replaced daily, for 2 days, with fresh MEM α 2000 medium supplemented with 10% of fetal calf serum (inactivated at 56° C.), 2 g/l of glucose, 15 mg/l of hypoxanthine, 10 mg/l of thymidine, 250 mg/l of xanthine, 0.2 mg/l of aminopterin, 25 mg/l of mycophenolic acid and 2 mM of glutamine.

The culture supernatant is then recovered and purified as described in Example 11. The amount of gp160 variant present in the supernatant after precipitation with $ZnCl_2$ is comparable to that found in the culture supernatant; in contrast, the amount of total proteins decreased substantially thus indicating that a large proportion of the contaminant protein is removed.

I claim:

1. A process for purifying a highly glycosylated protein from a crude preparation derived from a culture of eukaryotic cells, which comprises the action (i) of adding to said preparation a divalent metal ion in a sufficient amount in order to form a mixture which precipitates and (ii) after precipitation, of harvesting said protein from the mixture supernatant.

2. The process as claimed in claim 1, for purifying a highly glycosylated protein from a crude preparation which is an acellular extract derived from a cell culture, which comprises the action (i) of adding to said preparation a divalent metal ion in a sufficient amount in order to form a mixture which precipitates and (ii) after precipitation, of harvesting said protein from the mixture supernatant.

3. The process as claimed in claim 2, for purifying a highly glycosylated protein from a crude preparation which is an acellular extract derived from a culture of cells infected with a vaccinia virus expressing said highly glycosylated protein, which comprises the action (i) of adding to said preparation a divalent metal ion in a sufficient amount in order to form a mixture which precipitates and (ii) after precipitation, of harvesting said protein from the mixture supernatant.

4. The process as claimed in claim 1, for purifying from a crude preparation a protein whose glycosylation level is not less than 40%, which comprises the action (i) of adding to said preparation a divalent metal ion in a sufficient amount in order to form a mixture which precipitates and (ii) after precipitation, of harvesting said protein from the mixture supernatant.

5. The process as claimed in claim 1, for purifying a highly glycosylated protein from a crude preparation, which comprises the action of adding to said preparation a divalent metal ion in order to form a mixture in which the metal ion is at a final concentration of not less than 10 mM.

6. The process as claimed in claim 5, for purifying a highly glycosylated protein from a crude preparation, which comprises the action of adding to said preparation a divalent metal ion in order to form a mixture in which the metal ion is at a final concentration of not less than 20 mM.

7. The process as claimed in claim 1, for purifying a highly glycosylated protein from a crude preparation, which comprises the action of adding to said preparation a divalent metal ion selected from zinc, copper, cobalt, calcium or nickel.

8. The process as claimed in claim 1, for purifying a highly glycosylated protein from a crude preparation, which comprises the action of adding to said preparation a divalent metal ion in the form of a salt.

9. The process of claim 8 wherein said divalent metal ion salt is selected from the group consisting of $ZnCl_2$, $CuSO_4$, $CoSO_4$, $NiSO_4$ and $CaCl_2$.

10. The process as claimed in claim 1, in which the highly glycosylated protein is the protein gp120 from the HIV virus.

11. The process as claimed in claim 1, in which the highly glycosylated protein is a soluble variant of the protein gp160 from the HIV virus.

12. The process for purifying or concentrating a poxvirus from a preparation, which comprises the action (i) of adding to said preparation a divalent metal ion in a sufficient amount in order to form a mixture which precipitates and (ii) after precipitation, of harvesting said poxvirus in the form of a precipitate.

13. The process of claim 1 wherein the highly glycosylated protein comprises a glycosylation of not less than 30%.

14. The process of claim 1 wherein the heavily glycosylated protein is selected from the group consisting of fetuin, gp120, gp160, human interleukin 2, glycophorin and acid alpha-1-glycoprotein.

15. The process of claim 1 wherein said culture of eukaryotic cells comprises a yeast or mammalian cell culture.

16. The process of claim 15 wherein said culture of eukaryotic cells comprises CHO cells.

17. The process of claim 1 wherein the highly glycosylated protein is heterogeneously or homogeneously glycosylated.

* * * * *